United States Patent

Shimizu et al.

[11] Patent Number: 5,830,693
[45] Date of Patent: Nov. 3, 1998

[54] GENE ENCODING A REGULATORY FACTOR INVOLVED IN ACTIVATING EXPRESSION OF THE NITRILASE GENE PROMOTER

[75] Inventors: Sakayu Shimizu; Michihiko Kobayashi, both of Kyoto, Japan

[73] Assignee: Nitto Chemical Industry Co., Ltd., Tokyo, Japan

[21] Appl. No.: 683,908

[22] Filed: Jul. 19, 1996

[30] Foreign Application Priority Data

Jul. 21, 1995 [JP] Japan .................................. 7-185626

[51] Int. Cl.$^6$ ............................. C12N 9/15; C12N 9/78; C12N 15/31; C12P 7/40

[52] U.S. Cl. ................. 435/69.1; 435/71.2; 435/136; 435/169; 435/172.3; 435/227; 435/252.3; 435/320.1; 530/350; 536/23.1; 536/23.74

[58] Field of Search .......................... 530/350; 536/23.1, 536/23.74; 435/320.1, 252.3, 172.3, 69.1, 169, 227, 71.2, 136

[56] References Cited

U.S. PATENT DOCUMENTS 4,652,639  3/1987  Stabinsky .............................. 435/91.52

FOREIGN PATENT DOCUMENTS 0502476  9/1992  European Pat. Off. .
0719862  7/1996  European Pat. Off. .

OTHER PUBLICATIONS

Komeda et al., Proc. Natl. Acad. Sci. USA 93(20):10572–10577 (1996).

"Nitrilase from Rhodococcus rhodochrous J1" *The Journal of Biological Chemistry*, vol. 267, No. 29, pp. 20746–20751, Michihiko Kobayashi, et al.

"Transcriptional regulation of the Rhodococcus rhodochrous J1 nitA gene encoding a nitrilase" *Proc. Natl. Acad. Sci. USA*, vol. 93, pp. 10572–10577, Oct. 1996, Hidenobu Komeda, et al.

*Primary Examiner*—Johnny F. Railey, II
*Attorney, Agent, or Firm*—Steinberg, Raskin & Davidson, P.C.

[57] ABSTRACT

The invention relates to a regulatory factor substantially containing an amino acid sequence represented by SEQ ID NO:1 and having the action of activating a nitrilase gene promoter, a regulatory factor gene containing DNA coding substantially for said regulatory factor, a recombinant plasmid containing said regulatory factor gene, a nitrilase gene containing a promoter region and a DNA region capable of replicating in a microorganism belonging to the genus Rhodococcus, and a transformant transformed with said recombinant plasmid.

17 Claims, 1 Drawing Sheet

5,830,693

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 319 AMINO ACID RESIDUES
        ( B ) TYPE: AMINO ACID
        ( D ) TOPOLOGY: LINEAR ( i i ) MOLECULE TYPE: PROTEIN ( v i ) ORIGINAL SOURCE:
        ( A ) ORGANISM: Rhodococcus rhodochrous
        ( B ) INDIVIDUAL ISOLATE: J1
        ( C ) CELL TYPE: unicellular organism ( x i ) SEQUENCE DESCRIPTION: SEQ ID NO:1:

```
Met Asn Thr Phe Phe Ser Ser Asp Gln Val Ser Ala Pro Asp Arg Val
  1               5                  10                  15

Ala Leu Trp His Asp Val Ile Cys Arg Ser Tyr Val Pro Leu Asn Ile
             20                  25                  30

Thr Leu Thr Ser Glu Gln Pro Phe Ile Gly Thr Val Ser Thr Gly Asn
             35                  40                  45

Leu Gly Thr Val Arg Ile Ala Thr Ser Ser Ser Leu Pro Gln Gln Ile
     50                  55                  60

Thr Arg Thr Arg Arg Leu Ile Arg Gln Asp Glu Arg Glu Tyr Leu Met
 65                  70                  75                  80

Val Gly Val Gln Ser Ala Gly His Ala Leu Val Gln Gln His Gly Arg
                 85                  90                  95

Thr Ala Arg Val Gly Arg Gly Gly Leu Val Phe Trp Asp Thr Arg His
                100                 105                 110

Pro Tyr Asp Ile Leu Phe Pro Thr Asp Trp Arg Met Ser Val Phe Gln
             115                 120                 125

Phe Pro Arg Tyr Ser Phe Gly Phe Thr Glu Asp Phe Ile Gly Arg Met
     130                 135                 140

Thr Ala Val Asn Val Gly Gly Asp Arg Gly Ile Gly Arg Val Val Ser
145                 150                 155                 160

Ser Phe Met Thr Ser Ile Asn Asp Ala Thr Asp Ala Gly Asp Leu Ala
                 165                 170                 175

Glu Val Ala Ser Leu His Asn Ser Ala Val Asp Leu Leu Ser Ala Ala
             180                 185                 190

Ile Arg Thr Glu Leu Ala Asp Gln Ala Ala Ala Ser Asp Gly Leu Leu
             195                 200                 205

Glu Cys Val Leu Ala Tyr Ile Arg Gln Asn Leu Ala Asp Pro Asn Leu
     210                 215                 220

Cys Ala Ser Gln Ile Ala Ala Glu His Asn Val Ser Val Arg Thr Leu
225                 230                 235                 240
```

-continued

| His | Arg | Leu | Phe | Ser | Ala | Thr | Gly | Gln | Gly | Val | Ala | Glu | His | Ile | Arg |
|     |     |     |     | 245 |     |     |     |     | 250 |     |     |     |     | 255 |     |

| Asn | Leu | Arg | Leu | Glu | Arg | Ile | Lys | Thr | Glu | Leu | Ala | Asp | Pro | Thr | Ser |
|     |     |     | 260 |     |     |     |     | 265 |     |     |     |     | 270 |     |     |

| Arg | Arg | Tyr | Thr | Ile | Ser | Ala | Leu | Ala | Arg | Lys | Trp | Gly | Phe | Leu | Asp |
|     |     | 275 |     |     |     |     | 280 |     |     |     |     | 285 |     |     |     |

| Pro | Ser | Thr | Phe | Ser | Arg | Ala | Phe | Lys | Asp | Ala | Tyr | Gly | Ile | Thr | Ala |
|     | 290 |     |     |     |     | 295 |     |     |     |     | 300 |     |     |     |     |

| Arg | Glu | Trp | Ala | Ala | Ser | Ala | Ser | Ala | Ser | Pro | Thr | Glu | Val | Ser |
| 305 |     |     |     |     | 310 |     |     |     |     | 315 |     |     |     | 319 |

( 2 ) INFORMATION FOR SEQ ID NO:2:

( i ) SEQUENCE CHARACTERISTICS:
        ( A ) LENGTH: 960 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Rhodococcus rhodochrous
        ( B ) INDIVIDUAL ISOLATE: J1
        ( C ) CELL TYPE: unicellular organism ( x i ) SEQUENCE DESCRIPTION: SEQ ID NO:2:

| ATG | AAC | ACT | TTC | TTC | TCC | TCA | GAC | CAG | GTC | TCG | GCG | CCC | GAT | CGC | GTC | 48 |
| GCG | CTC | TGG | CAC | GAT | GTC | ATC | TGC | CGT | AGC | TAT | GTC | CCG | CTC | AAC | ATC | 96 |
| ACC | CTC | ACG | AGC | GAG | CAA | CCC | TTC | ATC | GGT | ACG | GTC | TCG | ACG | GGC | AAC | 144 |
| TTG | GGC | ACG | GTA | CGT | ATC | GCG | ACG | TCC | TCG | TCA | CTG | CCC | CAA | CAG | ATC | 192 |
| ACC | CGC | ACT | CGT | CGC | TTG | ATC | AGG | CAG | GAC | GAG | CGT | GAG | TAC | CTC | ATG | 240 |
| GTT | GGG | GTG | CAG | TCC | GCC | GGC | CAT | GCA | CTC | GTG | CAG | CAG | CAC | GGC | AGA | 288 |
| ACT | GCA | CGA | GTC | GGT | CGC | GGT | GGA | CTG | GTC | TTC | TGG | GAC | ACC | CGC | CAT | 336 |
| CCC | TAC | GAC | ATC | CTC | TTT | CCG | ACA | GAC | TGG | AGG | ATG | AGC | GTA | TTC | CAG | 384 |
| TTC | CCG | CGA | TAC | TCT | TTC | GGC | TTC | ACC | GAA | GAC | TTC | ATC | GGC | AGG | ATG | 432 |
| ACC | GCG | GTG | AAC | GTC | GGG | GGC | GAT | CGC | GGT | ATC | GGC | CGA | GTG | GTT | TCA | 480 |
| TCC | TTC | ATG | ACA | AGC | ATC | AAC | GAT | GCG | ACC | GAC | GCA | GGA | GAC | TTG | GCG | 528 |
| GAG | GTA | GCT | TCA | CTC | CAC | AAC | AGT | GCT | GTC | GAT | CTT | CTG | TCA | GCG | GCG | 576 |
| ATA | CGG | ACC | GAG | CTT | GCC | GAT | CAA | GCC | GCC | GCC | TCC | GAC | GGC | CTA | CTC | 624 |
| GAG | TGT | GTG | CTC | GCG | TAT | ATC | CGA | CAG | AAC | CTG | GCC | GAC | CCG | AAC | CTG | 672 |
| TGT | GCC | TCA | CAG | ATC | GCG | GCG | GAA | CAC | AAC | GTC | TCT | GTG | CGG | ACC | CTC | 720 |
| CAC | CGA | CTG | TTC | TCG | GCC | ACG | GGA | CAG | GGC | GTG | GCC | GAA | CAC | ATC | CGT | 768 |
| AAC | CTC | CGA | CTC | GAG | CGC | ATC | AAG | ACT | GAG | CTG | GCA | GAC | CCA | ACG | AGC | 816 |
| CGG | CGA | TAT | ACG | ATC | AGC | GCT | TTG | GCG | AGA | AAA | TGG | GGG | TTC | CTC | GAT | 864 |
| CCC | TCA | ACG | TTC | TCA | CGC | GCG | TTC | AAA | GAC | GCC | TAC | GGC | ATC | ACT | GCC | 912 |
| CGA | GAG | TGG | GCG | GCT | TCT | GCA | TCA | GCA | TCA | CCG | ACG | GAG | GTT | TCG | TAG | 960 |

( 2 ) INFORMATION FOR SEQ ID NO:3:

( i ) SEQUENCE CHARACTERISTICS:
        ( A ) LENGTH: 1390 base pairs
        ( B ) TYPE: nucleic acid
        ( C ) STRANDEDNESS: double -continued (D) TOPOLOGY: linear (ii) MOLECULE TYPE: DNA (genomic)

(vi) ORIGINAL SOURCE:
    (A) ORGANISM: Rhodococcus rhodochrous
    (B) INDIVIDUAL ISOLATE: J1
    (C) CELL TYPE: unicellular organism (xi) SEQUENCE DESCRIPTION: SEQ ID NO:3:

| | | | | | | |
|---|---|---|---|---|---|---|
| CGATCGCAGC | GAGGCTGCCC | GCCGGTAACC | CCGATAGGTC | CACACCACGT | ATCCGGCGG | 60 |
| TTACACCTTC | TCGACAGGGG | CAATCGAGAC | CGAGCCCGGC | ATCGCGATTA | CGGCTACCCT | 120 |
| GAAAAGAGCA | ATGAACGGGG | TGAGCACCAG | GTAGGTCGAT | GAACACTTTC | TTCTCCTCAG | 180 |
| ACCAGGTCTC | GGCGCCCGAT | CGCGTCGCGC | TCTGGCACGA | TGTCATCTGC | CGTAGCTATG | 240 |
| TCCCGCTCAA | CATCACCCTC | ACGAGCGAGC | AACCCTTCAT | CGGTACGGTC | TCGACGGGCA | 300 |
| ACTTGGGCAC | GGTACGTATC | GCGACGTCCT | CGTCACTGCC | CCAACAGATC | ACCCGCACTC | 360 |
| GTCGCTTGAT | CAGGCAGGAC | GAGCGTGAGT | ACCTCATGGT | TGGGGTGCAG | TCCGCCGGCC | 420 |
| ATGCACTCGT | GCAGCAGCAC | GGCAGAACTG | CACGAGTCGG | TCGCGGTGGA | CTGGTCTTCT | 480 |
| GGGACACCCG | CCATCCCTAC | GACATCCTCT | TCCCGACAGA | CTGGAGGATG | AGCGTATTCC | 540 |
| AGTTCCCGCG | ATACTCTTTC | GGCTTCACCG | AAGACTTCAT | CGGCAGGATG | ACCGCGGTGA | 600 |
| ACGTCGGGGG | CGATCGCGGT | ATCGGCCGAG | TGGTTTCATC | CTTCATGACA | AGCATCAACG | 660 |
| ATGCGACCGA | CGCAGGAGAC | TTGGCGGAGG | TAGCTTCACT | CCACAACAGT | GCTGTCGATC | 720 |
| TTCTGTCAGC | GGCGATACGG | ACCGAGCTTG | CCGATCAAGC | CGCCGCCTCC | GACGGCCTAC | 780 |
| TCGAGTGTGT | GCTCGCGTAT | ATCCGACAGA | ACCTGGCCGA | CCCGAACCTG | TGTGCCTCAC | 840 |
| AGATCGCGGC | GGAACACAAC | GTCTCTGTGC | GGACCCTCCA | CCGACTGTTC | TCGGCCACGG | 900 |
| GACAGGGCGT | GGCCGAACAC | ATCCGTAACC | TCCGACTCGA | GCGCATCAAG | ACTGAGCTGG | 960 |
| CAGACCCAAC | GAGCCGGCGA | TATACGATCA | GCGCTTTGGC | GAGAAAATGG | GGGTTCCTCG | 1020 |
| ATCCCTCAAC | GTTCTCACGC | GCGTTCAAAG | ACGCCTACGG | CATCACTGCC | CGAGAGTGGG | 1080 |
| CGGCTTCTGC | ATCAGCATCA | CCGACGGAGG | TTTCGTAGGA | AGAGCCCGGT | CTCCGGCCTG | 1140 |
| CCCTTGTTCG | CTTGCGCACC | GTTCGGTCCG | TCGCTTCCGA | TGAAGCCGGA | GCCGGCAGGT | 1200 |
| TGGCTTCCTC | CCGCGATCCG | ATCGCTCGGG | GATTGTCCGG | GGCACCGCTG | GTGACCTCCA | 1260 |
| GTGCTGCTCC | GGCCTGGTGT | CCGCGATCGG | TGTGCCCCTG | CCCCGATGCA | TCCGGGCCGT | 1320 |
| GATGCCAGTG | CTCGGCAGGA | CCCACCGGCG | ACGACGGCCA | GCATGACCCA | TGGACCGGTC | 1380 |
| GGTCGAATTC | | | | | | 1390 |

GENE ENCODING A REGULATORY FACTOR INVOLVED IN ACTIVATING EXPRESSION OF THE NITRILASE GENE PROMOTER

FIELD OF THE INVENTION

The present invention relates to a regulatory factor involved in expression of a nitrilase gene as well as to DNA coding for said regulatory factor. In particular, the present invention relates to a regulatory factor derived from Rhodococcus rhodochrous J1 and having the action of activating a nitrilase gene promoter, a recombinant plasmid containing DNA coding for said regulatory factor, a nitrilase gene promoter and a nitrilase gene, and a transformant transformed with said recombinant plasmid.

BACKGROUND OF THE INVENTION

Organic acids can be formed from their corresponding nitrites under mild conditions by use of microorganisms or microorganism-derived enzymes (e.g. nitrilase) as catalysts (see Japanese Unexamined Patent Publication (hereinafter referred to as "Kokai") Nos. Sho 58-201992, Sho 61-40795, and U.S. Pat. No. 5,283,193 (Hei 2-84198 and Hei 3-251192).

As compared with conventional processes, the catalytic ability of microorganisms to hydrolyze nitrites is expected to be drastically improved by use of recombinants carrying a cloned nitrilase gene because they can be engineered to contain multiple copies of the gene.

In order to prepare a microorganism as a catalyst having higher catalytic activity, the present inventors cloned a nitrilase gene from Rhodococcus rhodochrous J1 and constructed a plasmid by inserting the gene to a region downstream of E. coli lactose promoter (J. Biol. Chem. 267, 20746–20751 (1992)). E. coli into which said plasmid had been introduced exhibited higher nitrilase activity when cultured in the presence of IPTG (isopropyl-β-D-thiogalactoside).

To further improve a bacterial catalyst for utility value, a recombinant was prepared from a microorganism belonging to the genus Rhodococcus with superior functions by integrating a nitrilase gene region into a Rhodococcus-E. coli hybrid plasmid vector (see Kokai Nos. Hei 5-64589 (=EP 0502476A) and 5-68566 (=EP 0502476A)) and introducing it into a microorganism belonging to the genus Rhodococcus.

However, no nitrilase activity was attained by the transformant into which the nitrilase gene region had merely been introduced.

Hence, it was desired to develop a transformant of the genus Rhodococcus by which nitrilase activity can be obtained.

SUMMARY OF THE INVENTION

The object of the present invention is to provide a regulatory factor derived from Rhodococcus rhodochrous J1 and having the action of activating a nitrilase gene promoter, a recombinant plasmid containing DNA coding for said regulatory factor, a nitrilase gene promoter and a nitrilase gene, and a transformant transformed with said recombinant plasmid.

The present inventors speculated that the reason the gene is not expressed by the transformant derived from the genus Rhodococcus is that the promoter for the nitrilase gene fails to function because the transformant does not carry a gene coding for a regulatory factor necessary for functioning of the promoter. Hence, they thought that a gene coding for such regulatory factor is present somewhere in chromosomal DNA from the J1 strain and found the gene located downstream of the nitrilase structural gene. As a result of preparation of a transformant belonging to the genus Rhodococcus carrying this gene, the transformant could successfully express nitrilase with high activity.

That is, the present invention is a regulatory factor substantially containing an amino acid sequence represented by SEQ ID NO:1 and having the action of activating a nitrilase gene promoter. This action of the regulatory factor is enhanced by the presence of nitriles such as isovaleronitrile.

Further, the present invention is a regulatory factor gene containing DNA coding substantially for an amino acid sequence represented by SEQ ID NO:1.

Further, the present invention is a recombinant plasmid containing said regulatory factor gene, a nitrilase gene containing a promoter region, and a DNA region capable of replicating in a microorganism belonging to the genus Rhodococcus. As the DNA region capable of replicating in a microorganism belonging to the genus Rhodococcus, mention may be made of a member selected from a group consisting of plasmids pRC001, pRC002, pRC003 and pRC004.

The terms "substantially containing" and "coding substantially for" an amino acid sequence are intended to indicate that insofar as the peptide of the amino acid sequence maintains the function of activating the nitrilase gene promoter, the amino acid sequence may have deletion, replacement, addition etc. of amino acids. Hence, an amino acid sequence represented by SEQ ID NO:1 but with deletion etc. of the 1st amino acid methionine (Met) is understood as an intended polypeptide with an alternation of amino acid. Further, the present DNA coding for such polypeptide, which is represented by a nucleotide sequence represented by SEQ ID NO:2, includes degenerated isomers coding for the same polypeptide with different degenerated codons.

Further, the present invention is a transformant transformed with said recombinant plasmid.

DETAILED DESCRIPTION OF THE INVENTION

Figure 1:
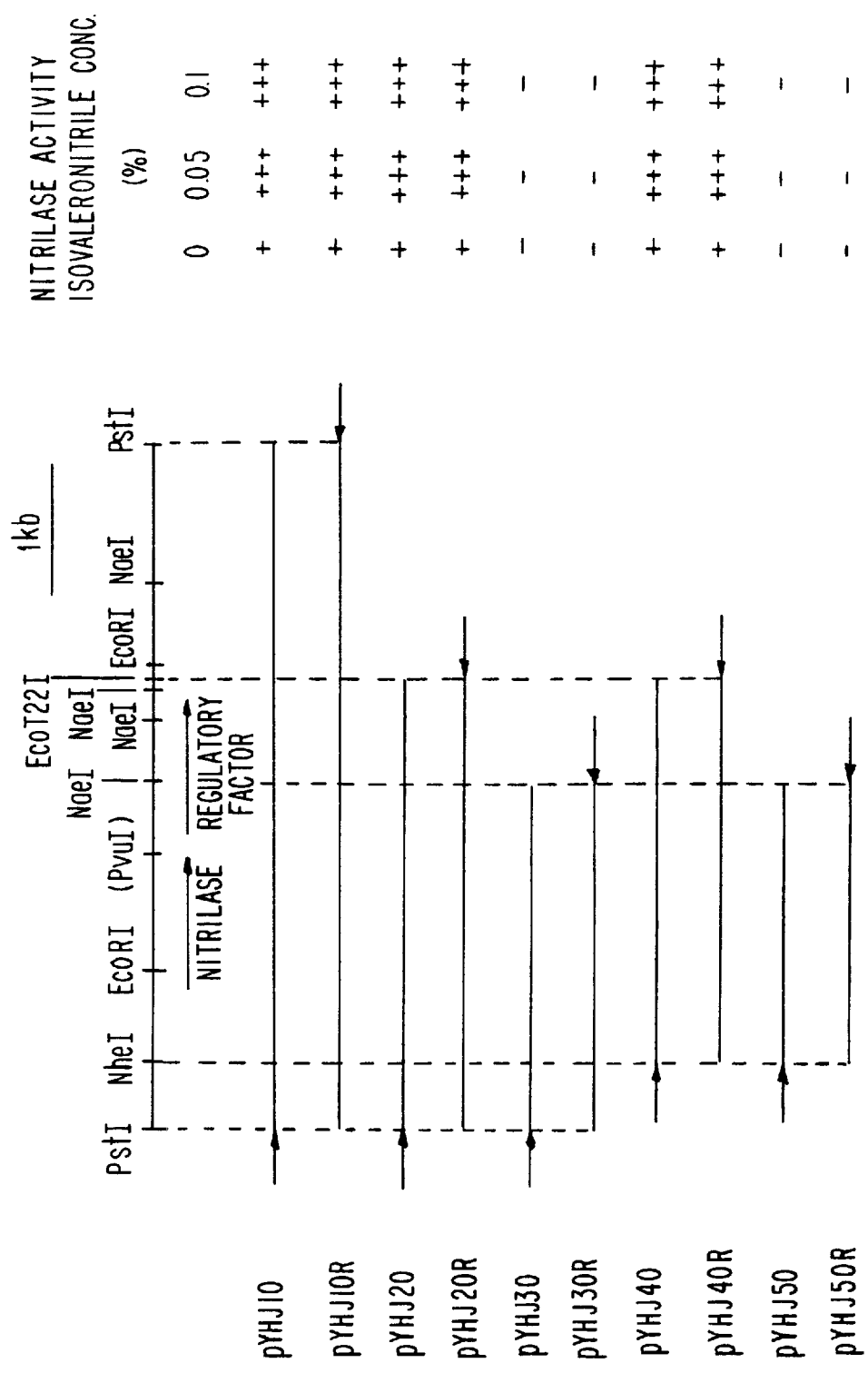
FIG. 1 shows a restriction enzyme map in the vicinity of the nitrilase gene from the J1 strain, plasmids constructed in the present invention, and nitrilase activities of transformants carrying these plasmids.

The gene of the present invention contains a region coding for a regulatory factor having the action of activating a nitrilase gene promoter (referred to hereinafter as "regulatory factor") and it is prepared in the following steps.

(1) Construction of a plasmid containing a nitrilase gene and a gene coding for the regulatory factor:

The nitrilase gene derived from Rhodococcus rhodochrous J1 (referred to hereinafter as "the J1 strain") is known (J. Biol. Chem.267, 20746–20751 (1992)) and obtained as plasmid pNJ10 having this gene inserted into vector pUC19. The nitrilase gene can be prepared by digesting this plasmid PNJ10 with suitable restriction enzymes such as PstI etc. The nitrilase gene and the gene coding for the regulatory factor are included in the gene fragment thus prepared.

A plasmid for use in ligation of this gene fragment containing the nitrilase gene includes e.g. hybrid plasmids such as pK1, pK2, pK3 and pK4.

The plasmid pK1 is a hybrid plasmid between plasmid vector pHSG299 for *E. coli* and plasmid pRC001 which is a DNA region capable of replicating in a microorganism belonging to the genus Rhodococcus. Hybrid plasmids between plasmid vector pHSG299 and plasmids pRC002, pRC003 and pRC004 are designated pK2, pK3 and pK4 respectively (see Kokai No. Hei 5-68566). In the present invention, the hybrid vector pK4 will be exemplified.

Then, the above fragment containing the nitrilase gene and the gene coding for the regulatory factor is ligated to the aforementioned hybrid plasmid. Ligation may be carried out in any known method. For example, a commercially available ligation kit (Takara ligation kit available from Takara Shuzo Co., Ltd.) can be used in ligation.

The plasmid DNA thus obtained contains the nitrilase gene and the gene coding for the regulatory factor, but where the gene coding for the regulatory factor is located in this plasmid DNA is not certain.

Hence, this plasmid DNA is treated with various restriction enzymes to prepare DNA fragments varying in size which are transformed into microorganisms belonging to the genus Rhodococcus. The location of the gene coding for the regulatory factor can be determined on the basis of the sizes of DNA fragments permitting the transformants to express nitrilase.

The gene fragment containing the nitrilase gene and the gene coding for the regulatory factor can be ligated to said plasmid in the correct direction or reverse direction in 50% probability.

The J1 strain has been deposited as FERM BP-1478 with the National Institute of Bioscience and Human-Technology, Agency of Industrial Science and Technology, Japan. The plasmid pNJ10 containing the nitrilase gene and the gene coding for the regulatory factor has been deposited as recombinant *E. coli* JM109/pNJ10 (FERM BP-5548) and the hybrid plasmid vector pK4 has been deposited as recombinant *R. rhodochrous* ATCC 12674/pK4 (FERM BP-3731) containing the same.

(2) Preparation of a transformant of the genus Rhodococcus and measurement of nitrilase activity The plasmid DNA prepared in (1) above is introduced to a microorganism belonging to the genus Rhodococcus e.g. *Rhodococcus rhodochrous* (ATCC12674). That is, *Rhodococcus rhodochrous* (ATCC12674) at the logarithmic growth phase is harvested by centrifugation, washed and mixed with the plasmid DNA. Then, a known method e.g. electroporation etc. is used to introduce the plasmid DNA into the microorganism. The screening of the transformants can be carried out by culturing them in kanamycin-containing medium, and the target transformant can be obtained as a kanamycin-resistant colony.

Then, the resulting transformant is cultured in conventional medium containing polypeptone, yeast extract, malt extract etc. to give a bacteria suspension, then benzonitrile is added to the suspension as a substrate for nitrilase, and benzoic acid formed is determined in HPLC etc. If the nitrilase gene is successfully expressed, benzonitrile is converted into benzoic acid by the action of the nitrilase produced. The presence or absence of the expression of the regulatory factor gene (the activation of the nitrilase gene promoter) can be confirmed in terms of the expression of the nitrilase gene by examining the presence or absence of the formation of benzoic acid.

Isovaleronitrile, known as a good inducer for the J1 strain nitrilase, can further be added to attain higher nitrilase activity.

(3) Nucleotide sequencing

The gene is obtained from the transformant whose activity was observed in (2) above, and its nucleotide sequence is determined. Nucleotide sequencing can be effected using any of the known methods, e.g. the chain termination method (Sanger F., Science,214, 1205–1210 (1980)).

The nucleotide sequence (1286 bp) between the BsmI site of the nitrilase gene and the PvuI site downstream of the gene has already been revealed in the gene thus obtained (J. Biol. Chem. 267, 20746–20751 (1992)), and thus the nucleotide sequence from the PvuI site to the EcoRI site further downstream of the gene is determined. The amino acid sequence of the regulatory factor of the present invention can be deduced from the determined nucleotide sequence.

EFFECT OF THE INVENTION

According to the present invention, there are provided a regulatory factor having the action of activating a nitrilase gene promoter, a gene containing DNA coding substantially for said regulatory factor, a recombinant plasmid containing said gene, and a transformant transformed with said plasmid.

Nitrilase is produced by said transformant. The regulatory gene and the nitrilase gene promoter can also be used in highly expressing other kinds of protein.

PREFERRED EMBODIMENTS OF THE INVENTION

Hereinafter, the present invention will be illustrated in detail by reference to the following example, which however is not intended to limit the scope of the invention.

The following abbreviations are used in the example. TE: 10 mM Tris-HCl (pH 7.8)-1 mM EDTA (pH 8.0). MY medium: 1% polypeptone, 0.3% yeast extract, 0.3% malt extract, 1% glucose.

EXAMPLE 1

(1) Construction of a plasmid containing a nitrilase gene and a regulatory gene

From a plasmid containing a nitrilase gene fragment from the J1 strain, said gene fragment (5.4 kbPstI fragment) was excised and inserted into the PstI site of the hybrid plasmid vector pK4 whereby a recombinant plasmid was constructed. Other plasmids were also prepared by inserting a partial region from the 5.4 kb PstI fragment into pK4. The detailed procedures are as follows.

First, the 5.4 kb PstI fragment was excised from plasmid pNJ10 obtained by inserting the 5.4 kb PstI fragment containing the nitrilase gene from the J1 strain into vector pUC19 (J. Biol. Chem.267, 20746–20751 (1992)).

Separately, PstI-cleaved pK4 was prepared in the following manner. Three microliters of reaction buffer (10 X ), 2 $\mu$l of restriction enzyme PstI and 15 $\mu$l of sterilized water were added to 10 $\mu$l of pK4 and the mixture was allowed to react 37° C. for 2 hours. After an equal amount of TE-saturated phenol was added to the reaction solution, the solution was stirred and separated into upper (aqueous) and lower layers by centrifugation. The upper layer was extracted again with TE-saturated phenol in the same manner and further extracted twice with an equal amount of chloroform in the same manner. Three microliters of 3M sodium acetate and 90 $\mu$l of ethanol were added to the upper layer, and the sample was allowed to stand at −80° C. for 30 minutes, centrifuged, dried and dissolved in TE.

Then, 3 $\mu$l of the DNA fragment fraction containing the 5.4 kb PstI fragment was allowed to react with 1 $\mu$l of the above PstI-cleaved pK4 overnight at 4° C. using Takara ligation kit (available from Takara Shuzo Co., Ltd.), whereby the 5.4 kb PstI fragment was inserted into pK4. After the reaction was finished, the reaction solution was transformed into *E. coli* JM109. From the transformants thus obtained, plasmids pYHJ10 and pYHJ10R were prepared by the method of Birnboim and Doly (Nucleic Acids Res. 7, 1513 (1979)). The plasmid pYJ10R contained the insert in the reverse direction.

Plasmids pYHJ20 to pYHJ50 containing a partial region from the 5.4 kb PstI fragment and plasmids pYHJ20R to pYHJ50R containing the corresponding insert in the reverse direction were constructed in the same manner.

The restriction enzyme and means used were as follows:
pYHJ20 and pYHJ20R:
  Pst-EcoT22I fragment was inserted into the PstI site of pK4.
pYHJ30 and pYHJ30R:
  Plasmid pNJ10 was digested with PstI and then blunt-ended with T4 DNA polymerase. It was then cleaved with NaeI, and the fragment was separated and recovered by electrophoresis (0.7% agarose). Separately, pK4 was cleaved with PstI and then blunt-ended with T4 DNA polymerase, and the above fragment was inserted into the resulting blunt end.
pYHJ40 and pYHJ40R:
  Plasmid PNJ10 was cleaved with NheI and EcoT22I and blunt-ended with T4DNA polymerase. The fragment was separated and recovered by electrophoresis (0.7% agarose). Separately, pK4 was cleaved with PstI and then blunt-ended with T4 DNA polymerase, and the above fragment was inserted into the resulting blunt end.
pYHJ50 and pYHJ50R:
  Plasmid PNJ1O was cleaved with NheI and blunt-ended with T4 DNA polymerase. It was then cleaved with NaeI, and the fragment was separated and recovered by electrophoresis (0.7% agarose). Separately, pK4 was cleaved with PstI and then blunt-ended with T4 DNA polymerase, and the above fragment was inserted into the resulting blunt end.

(2) Preparation of a transformant of the genus Rhodococcus and determination of nitrilase activity The respective plasmids thus obtained were introduced into *Rhodococcus rhodochrous* ATCC12674 and the resulting transformants were examined for their nitrilase activity.

The introduction of the plasmids into the microorganism was carried out as follows: Rhodococcus rhodochrous ATCC12674 at the logarithmic growth phase was harvested by centrifugation, washed 3 times with ice-cold sterilized water and suspended in 15% PEG 6000 (polyethylene glycol 6000) to a final concentration of at least $10^9$ cells/ml. One microgram of plasmid DNA was mixed with 100 μl of the bacterial suspension and the mixture was cooled on ice. This mixture of DNA and bacteria was introduced into a gene pulser chamber, cooled on ice and pulsed with an electrostatic capacity of 25 μF, a resistance of 400Ω and a voltage of 20 kV/cm. The bacterial suspension thus treated was placed on ice for 10 minutes and heated at 37° C. for 5 minutes. One milliliter of MY medium was added to the suspension which was then shaken at 25° C. for 3 hours. The bacterial suspension was plated on an MY agar plate containing 50 μg/ml kanamycin and incubated at 28° C. for 2 days. The colony grown on the plate was plated on another MY agar plate containing kanamycin, and their resistance to kanamycin was ascertained by their growth on the plate.

The transformant of the genus Rhodococcus thus obtained was incubated at 28° C. for 2 days in a medium consisting of 10 g glycerol, 5 g polypeptone, 3 g yeast extract, 3 g malt extract, 1 g $KH_2PO_4$, 1 g $K_2HPO_4$, 0.01 g $CoCl_2 \cdot 6H_2O$ (pH 7.0)/1L medium. After isovaleronitrile (0.5 g/L and 1 g/L) known as a good inducer for the J1 nitrilase was added to it, the transformant was incubated in the same manner.

The bacterial cells were harvested by centrifugation, and the pellet was washed with 10 mM potassium phosphate buffer (pH 7.5) and then suspended in 0.1M potassium phosphate buffer (pH 7.5) containing 1 mM dithiothreitol.

Their nitrilase activity was determined as follows.

The bacterial suspension (0.25 ml) was diluted with a suitable amount of water, and 0.25 ml of 0.1 mM potassium phosphate buffer (pH 7.0) and 0.5 ml of 12 mM benzonitrile were added to it. They were allowed to react at 20° C. for 10 minutes and then 0.1 ml of 1N HCl was added to stop the reaction. The benzoic acid formed by the enzymatic reaction was analyzed by HPLC.

The results are shown in FIG. 1. In FIG. 1, the two arrows (large arrows) along the DNA fragment from the J1 strain indicate the location and direction of the nitrilase gene and the regulatory gene found in the present invention. The region assigned to each plasmid is the J1-derived DNA region inserted into vector pK4, and the arrows (small arrows) indicate the location and direction of the lac promoter on vector pK4.

The level of nitrilase activity in FIG. 1 is shown as "+" (weak) to "+++" (strongest). The symbol "−" indicates that no activity could be detected.

Nitrilase activity could be detected for the transformants carrying plasmids pYHJ10 and pYHJ10R, and particularly high activity was observed where isovaleronitrile was added. Similar results were obtained for plasmids lacking in a region 1.4 kb or further downstream from the nitrilase gene (pYHJ20 and pYHJ20R) and plasmids lacking in upstream and downstream regions of the nitrilase gene (pYHJ40 and pYHJ40R). However, no activity was detected for plasmids lacking in a region about 0.5 kb or further downstream from the nitrilase gene (pYHJ30 and pYHJ30R).

From the foregoing, it became evident that the gene for the regulatory gene is located in a downstream region very close to the nitrilase structural gene (see FIG. 1).

To determine which plasmid conferred the highest activity on the transformant, the transformants carrying pYHJ10R to pYHJ50R were examined for their nitrilase activity in the same manner as above.

The results are shown in Table 1. In Table 1, the transformant carrying pYHJ20R exhibited the highest activity.

TABLE 1

Nitrilase Activities of Transformants

| transformants | isovaleronitrile | protein conc. (mg/ml) | specific activity (U/mg) |
|---|---|---|---|
| ATCC12674/pK4 | − | 3.48 | N.D. |
|  | + | 2.03 | N.D. |
| ATCC12674/pYHJ10R | − | 2.52 | 0.003 |
|  | + | 4.26 | 0.193 |
| ATCC12674/pYHJ20R | − | 4.46 | 0.019 |
|  | + | 2.27 | 0.537 |
| ATCC12674/pYHJ30R | − | 4.46 | N.D. |
|  | + | 8.52 | N.D. |
| ATCC12674/pYHJ40R | − | 5.04 | 0.002 |
|  | + | 4.83 | 0.297 |
| ATCC12674/pYHJ50R | − | 4.61 | N.D. |
|  | + | 4.49 | N.D. |

N.D.: not detected.

(3) Nucleotide sequencing

Because the nucleotide sequence downstream from the nitrilase gene to the PvuI site was known (J. Biol. Chem.

267, 20746–20751 (1992)), about 1.4 kb nucleotide sequence from the PvuI site to the EcoRI site was determined. Nucleotide sequencing was carried out according to the chain termination method using Tth DNA polymerase (Sanger F., Science, 214, 1205–1210 (1980)).

The result is shown in SEQ ID NO:3. The analysis of the nucleotide sequence of SEQ. ID NO:3 revealed the presence of a single long open reading frame coding for the amino acid sequence of SEQ ID NO:1. The nucleotide sequence of the open reading frame is shown in SEQ ID NO:2. The amino acid sequence deduced from the nucleotide sequence of SEQ ID NO:2 is shown in SEQ ID NO:1.

Various publications are referenced herein, the disclosures of which are incorporated by reference herein in their entireties.

What is claimed is:

1. A regulatory factor substantially containing an amino acid sequence represented by SEQ ID NO:1 and having the action of activating a nitrilase gene promoter.

2. The regulatory factor according to claim 1 wherein the action of activating a nitrilase gene promoter is enhanced by the presence of a nitrile.

3. The regulatory factor according to claim 2 wherein the nitrile is isovaleronitrile.

4. A regulatory factor gene containing DNA coding substantially for an amino acid sequence represented by SEQ ID NO:1.

5. The regulatory factor gene according to claim 4 wherein the DNA coding substantially for an amino acid sequence represented by SEQ ID NO:1 is represented by SEQ ID NO:2.

6. A recombinant plasmid comprising:
   (a) a nitrilase gene promoter, a nitrilase gene, and a gene encoding the regulatory factor as in claim 4, wherein the nitrilase gene and the gene encoding the regulatory factor are expressed by the nitrilase gene promoter; and
   (b) a DNA region capable of replicating the plasmid in a microorganism belonging to the genus Rhodococcus.

7. The recombinant plasmid according to claim 6 wherein the DNA region capable of replicating in a microorganism belonging to the genus Rhodococcus is a member selected from a group consisting of plasmids pRC001, pRC002, pRC003, and pRC004.

8. A recombinant plasmid comprising:
   (a) a nitrilase gene promoter, a nitrilase gene, and a gene encoding the regulatory factor as in claim 5, wherein the nitrilase gene and the gene encoding the regulatory factor are expressed by the nitrilase gene promoter; and (b) a DNA region capable of replicating the plasmid in a microorganism belonging to the genus Rhodococcus.

9. A transformant transformed with the recombinant plasmid of claim 6.

10. A transformant transformed with the recombinant plasmid of claim 7.

11. A method of activating a nitrilase gene promoter for expression of nitrilase enzyme in a Rhodococcus host cell the method comprising transforming said host cell with the plasmid of any one of claims 6, 7 or 8 culturing the transformed cells in the presence of isovaleronitrile such that the regulatory factor is expressed and activates the nitrilase gene promoter resulting in expression of the nitrilase enzyme in the host cell.

12. The method of claim 11 wherein said regulatory factor gene is inserted downstream from said nitrilase gene.

13. The method of claim 11 wherein said SEQ ID NO: 1 is modified by the deletion of the first Met residue.

14. The method of claim 11 wherein said regulatory factor gene is a DNA molecule that comprises SEQ ID NO:2.

15. A method for producing an organic acid from a nitrile substrate comprising
 (a) transforming a Rhodococcus host cell with the plasmid of claim 6; and
 (b) culturing the transformant of (a) in the presence of a nitrile substrate precursor to an organic acid such that the expression of the regulatory factor and the nitrilase gene on the plasmid occurs, and the expressed nitrilase activity converts the nitrile substrate to an organic acid.

16. The method of claim 15 wherein the Rhodococcus host cell is *Rhodococcous rhodochrous*.

17. The method of claim 15 wherein said SEQ ID NO: 1 is modified by the deletion of the first Met residue.

* * * * *